United States Patent
Fujihashi et al.

(10) Patent No.: US 11,497,695 B2
(45) Date of Patent: Nov. 15, 2022

(54) ZINC OXIDE POWDER, DISPERSION, COMPOSITION, AND COSMETIC

(71) Applicant: SUMITOMO OSAKA CEMENT CO., LTD., Tokyo (JP)

(72) Inventors: Gaku Fujihashi, Tokyo (JP); Shingo Hosoda, Tokyo (JP); Kenichiro Nishida, Tokyo (JP); Syunsuke Suma, Tokyo (JP)

(73) Assignee: SUMITOMO OSAKA CEMENT CO., LTD., Tokyo (JP)

( * ) Notice: Subject to any disclaimer, the term of this patent is extended or adjusted under 35 U.S.C. 154(b) by 33 days.

(21) Appl. No.: 15/755,493

(22) PCT Filed: Aug. 25, 2016

(86) PCT No.: PCT/JP2016/074846
§ 371 (c)(1),
(2) Date: Feb. 26, 2018

(87) PCT Pub. No.: WO2017/038635
PCT Pub. Date: Mar. 9, 2017

(65) Prior Publication Data
US 2018/0256461 A1   Sep. 13, 2018

(30) Foreign Application Priority Data

Aug. 28, 2015 (JP) .............................. JP2015-169534
Nov. 26, 2015 (JP) .............................. JP2015-231151
Jan. 28, 2016 (JP) ................................. 2016-014678

(51) Int. Cl.
A61K 8/27 (2006.01)
A61Q 17/04 (2006.01)
A61K 8/04 (2006.01)
C01G 9/02 (2006.01)

(52) U.S. Cl.
CPC .................. *A61K 8/27* (2013.01); *A61K 8/04* (2013.01); *A61Q 17/04* (2013.01); *C01G 9/02* (2013.01); *C01P 2004/51* (2013.01); *C01P 2004/54* (2013.01); *C01P 2004/62* (2013.01); *C01P 2004/64* (2013.01); *C01P 2006/12* (2013.01); *C01P 2006/22* (2013.01); *C01P 2006/40* (2013.01)

(58) Field of Classification Search
CPC ... A61K 8/27; A61K 8/04; A01G 9/02; A61Q 17/04; C01G 9/02; C01P 2004/51; C01P 2004/54; C01P 2004/62; C01P 2004/64; C01P 2006/12; C01P 2006/22; C01P 2006/40

See application file for complete search history.

(56) References Cited

U.S. PATENT DOCUMENTS

| | | | |
|---|---|---|---|
| 4,808,398 A * | 2/1989 | Heistand, II | C01G 9/02 423/622 |
| 6,027,869 A * | 2/2000 | Maskasky | G03C 1/0051 430/567 |
| 7,670,676 B2 * | 3/2010 | Horiishi | A61K 49/1809 428/357 |
| 2004/0176498 A1 * | 9/2004 | Ando | C09D 11/16 523/160 |
| 2011/0150792 A1 * | 6/2011 | Shao | A61K 8/27 424/59 |
| 2012/0177707 A1 * | 7/2012 | Matsushita | A61K 8/11 424/401 |
| 2014/0212669 A1 | 7/2014 | Sueda et al. | |

FOREIGN PATENT DOCUMENTS

| | | |
|---|---|---|
| JP | 57-205319 A | 12/1982 |
| JP | 60-255620 A | 12/1985 |
| JP | 63-288913 A | 11/1988 |
| JP | 63-288914 A | 11/1988 |
| JP | 03-199121 A | 8/1991 |
| JP | 07-232919 A | 9/1995 |
| JP | 2002-201382 A | 7/2002 |
| JP | 2010-275223 A | 12/2010 |
| WO | 2016/143629 A1 | 9/2016 |

OTHER PUBLICATIONS

Sumicefine, Zinc Oxide for Cosmetics, pp. 1-2 (2013) (Year: 2013).*
Yin et al. (Chemosphere, online Dec. 2014, vol. 124, pp. 116-121) (Year: 2014).*
International Search Report for PCT/JP2016/074846 (dated Oct. 4, 2016).
Third Party Observation for PCT/JP2016/074846 (dated Aug. 3, 2017).
"Monodispersed Fine particles", vol. 34, Tadao Sugimoto, Journal of the Crystallographic Society of Japan, 1992.

* cited by examiner

*Primary Examiner* — Mark V Stevens
(74) *Attorney, Agent, or Firm* — Merchant & Gould P.C.

(57) ABSTRACT

Zinc oxide powder of the present invention contains zinc oxide particles, in which primary particles of the zinc oxide particles have a minor axis of 35 nm or more and 350 nm or less and have a Heywood diameter of 35 nm or more and 400 nm or less, and a coefficient of variation of a number distribution of the Heywood diameters of the primary particles of the zinc oxide powder is 50% or less.

16 Claims, No Drawings

ZINC OXIDE POWDER, DISPERSION, COMPOSITION, AND COSMETIC

TECHNICAL FIELD

The present invention relates to zinc oxide powder, a dispersion, a composition, and a cosmetic.

The present application is a National Stage Application under 35 U.S.C. § 371 of International Application No. PCT/JP2016/074846 filed on Aug. 25, 2016, which claims the benefit of priority to Japanese Patent Application No. 2015-169534 filed on Aug. 28, 2015, Japanese Patent Application No. 2015-231151 filed on Nov. 26, 2015, and Japanese Patent Application No. 2016-014678 filed on Jan. 28, 2016, the disclosures of all of which are hereby incorporated by reference in their entireties. The International Application was published in Japanese on Mar. 9, 2017 as WO 2017/038635.

BACKGROUND

Zinc oxide particles have an ultraviolet-shielding function, a gas transmission-suppressing function, and the like and are also highly transparent. Therefore, zinc oxide particles are used for applications requiring transparency such as ultraviolet-shielding films, ultraviolet-shielding glass, cosmetics, and gas barrier films (for example, refer to Patent Documents 1 to 8).

Zinc oxide particles are used after the particle diameters are adjusted depending on the applications. For example, Patent Document 5 proposes zinc oxide powder in which the average particle diameter is 0.01 µm or more and 0.03 µm or less so that high transparency and an ultraviolet absorption effect can be obtained at the same time.

In addition, Patent Document 8 proposes zinc oxide powder in which the average particle diameter is 0.2 µm or more and 0.3 µm or less in order to improve the long-wavelength ultraviolet ray (UVA)-shielding properties.

CITATION LIST

Patent Literature

[Patent Document 1] Japanese Laid-open Patent Publication No. 57-205319
[Patent Document 2] Japanese Laid-open Patent Publication No. 60-255620
[Patent Document 3] Japanese Laid-open Patent Publication No. 63-288913
[Patent Document 4] Japanese Laid-open Patent Publication No. 63-288914
[Patent Document 5] Japanese Laid-open Patent Publication No. 3-199121
[Patent Document 6] Japanese Laid-open Patent Publication No. 7-232919
[Patent Document 7] Japanese Laid-open Patent Publication No. 2002-201382
[Patent Document 8] Japanese Laid-open Patent Publication No. 2010-275223

SUMMARY OF INVENTION

Technical Problem

However, when the above-described zinc oxide powder is stored, there has been a problem in that the characteristics of the zinc oxide powder change and thus the storage stability deteriorates.

The present invention has been made in consideration of the above-described circumstances, and an object of the present invention is to provide zinc oxide powder having excellent storage stability, a dispersion, a composition, and a cosmetic which include the zinc oxide powder.

Solution to Problem

That is, a first aspect of the present invention is zinc oxide powder containing zinc oxide particles, in which primary particles of the zinc oxide particles have a minor axis of 35 nm or more and 350 nm or less and have a Heywood diameter of 35 nm or more and 400 nm or less, and a coefficient of variation of a number distribution of the Heywood diameters of the primary particles of the zinc oxide powder is 50% or less.

A second aspect of the present invention is a dispersion containing the zinc oxide powder of the first aspect of the present invention and a dispersion medium.

A third aspect of the present invention is a composition containing the zinc oxide powder of the first aspect of the present invention, a resin, and a dispersion medium.

A fourth aspect of the present invention is a cosmetic containing at least one of the zinc oxide powder of the first aspect of the present invention and the dispersion of the second aspect of the present invention.

Advantageous Effects of Invention

The zinc oxide powder of the present invention contains zinc oxide particles, in which the primary particles of the zinc oxide particles have a minor axis of 35 nm or more and 350 nm or less and a Heywood diameter (area circle-equivalent diameter) of 35 nm or more and 400 nm or less, and the coefficient of variation of the number distribution of the Heywood diameters of the primary particles of the zinc oxide powder is 50% or less. Therefore, the storage stability is excellent. In addition, the particles are large, and thus the ultraviolet-shielding effect is also strong.

The dispersion of the present invention contains the zinc oxide powder of the present invention and a dispersion medium. Therefore, it is possible to obtain dispersions having the same properties regardless of the storage period of the zinc oxide powder, and thus the quality stability is excellent.

The composition of the present invention contains the zinc oxide powder of the present invention, a resin, and a dispersion medium. Therefore, it is possible to obtain compositions having the same properties regardless of the storage period of the zinc oxide powder, and thus the quality stability is excellent.

The cosmetic of the present invention contains at least one selected from the zinc oxide powder of the present invention and the dispersion of the present invention. Therefore, it is possible to obtain cosmetics having the same properties regardless of the storage period of the zinc oxide powder, and thus the quality stability is excellent.

DESCRIPTION OF EMBODIMENTS

Preferred examples of zinc oxide powder, a dispersion, a composition, and a cosmetic of the present invention will be described.

Meanwhile, the following examples are simply specific descriptions for the better understanding of the gist of the present invention and do not limit the present invention unless particularly specified. Omission, addition, substitution, and other modification are possible within the scope of the gist of the present invention.

[Zinc Oxide Powder]

The zinc oxide powder of the present invention contains zinc oxide particles, in which the primary particles of the zinc oxide particles have a minor axis of 35 nm or more and 350 nm or less and have a Heywood diameter of 35 nm or more and 400 nm or less. The coefficient of variation of the number distribution of the Heywood diameters of the primary particles is 50% or less.

In addition, the zinc oxide powder of the present invention is preferably made only of zinc oxide particles, in which the primary particles of the zinc oxide particles have a minor axis of 35 nm or more and 350 nm or less and have a Heywood diameter of 35 nm or more and 400 nm or less. The coefficient of variation of the number distribution of the Heywood diameters of the primary particles of the zinc oxide powder is 50% or less.

As the definition of the particle diameter analysis of the zinc oxide powder of the present invention, the definition specified by Japanese Industrial Standards JIS Z 8827-1 "Particle size analysis Image analysis methods-Part 1: Static image analysis methods" is used. The particle diameters can be measured by analyzing the images of the particles using the method regulated by this standard.

In addition, the actual measurement of the particle diameters can be carried out using, for example, image analysis software Mac-View Ver. 4 (manufactured by Mountech Co., Ltd.) or the like, in which computation is carried out according to the present standard.

In the zinc oxide powder of the present invention, the minor axes of the primary particles of the zinc oxide particles and the major axes and Heywood diameters of the primary particles are values computed using images that are observed using an electronic microscope. In a case in which particles agglomerate together when observed using an electronic microscope, the minor axes of the primary particles, the major axes of the primary particles, and the Heywood diameters of the primary particles refer to values measured using a part that can be recognized as one particle.

In the zinc oxide powder of the present invention, the minor axes of the primary particles, the major axes of the primary particles, the Heywood diameters of the primary particles, and the aspect ratio of the primary particles refer to values obtained by measuring at least 100 primary particles, preferably 200 primary particles, more preferably 300 primary particles, and still more preferably 500 primary particles. In examples to be descried below, values obtained by measuring 200 particles will be used.

Meanwhile, the electronic microscope may be a transmission electron microscope or a scanning electron microscope. A transmission electron microscope is preferably used.

In the present invention, the primary particle can be considered as a particle that can be recognized as an individual particle having no boundaries (grain boundaries) therein, that is, a non-agglomerate in the case of being observed using an electron microscopic picture (magnification: 10,000 to 100,000 times). In other words, in a case in which agglomerates and primary particles coexist in a mixed form, the primary particle means a particle having the smallest outline.

(Minor Axes of Primary Particles)

In the zinc oxide powder of the present invention, the minor axis of the primary particle of the zinc oxide particle refers to the length of the short side of the rectangle in which the short side becomes shortest when rectangles circumscribing the primary particles are provided. Generally, a plurality of rectangles circumscribing the zinc oxide particles is present. Therefore, among the rectangles circumscribing the zinc oxide particles, the rectangle in which the short side becomes shortest is selected, and the short side of the rectangle is considered as the minor axis of the primary particle of the zinc oxide particle. Meanwhile, in a case in which rectangles circumscribing the primary particles become squares, the minor axis refers to the length of one side.

In the zinc oxide powder of the present invention, the major axes of the primary particles of the zinc oxide particles refer to the length of the long side of the rectangle in which the short side becomes shortest.

(Heywood Diameters and Aspect Ratios of Primary Particles)

In the zinc oxide powder of the present invention, the Heywood diameters of the primary particles of the zinc oxide particles refer to the diameter of a circle having the same area as the projected area of the primary particle.

(Aspect Ratios of Primary Particles)

In the zinc oxide powder of the present invention, the aspect ratio of the primary particle of the zinc oxide particle refers to a value obtained by dividing the major axis of the primary particle by the minor axis of the primary particle (the major axis of the primary particle/the minor axis of the primary particle).

(Methods for Obtaining Content Rate and Coefficient of Variation)

In the zinc oxide powder of the present invention, the content rate in the number distribution refers to a value obtained by converting the number distribution to a number-based distribution using geometric numerical values such as the minor axes of the primary particles of the zinc oxide particles, the major axes of the primary particles, the Heywood diameters of the primary particles, and the aspect ratio of the primary particles, which are obtained by evaluation in which the above-described image is used, and adding the corresponding particle diameters to the number-based distribution to be obtained. For example, the content rate of the minor axes of the primary particles of the zinc oxide particles can be considered as the fraction of the number of particles included in a specific particle size distribution, which is obtained when the obtained minor axes are converted to the number-based distribution.

In the zinc oxide powder of the present invention, the coefficient of variation of the number distribution of the Heywood diameters refers to a value (%) obtained by dividing the standard deviation of the Heywood diameters by the arithmetic value of the Heywood diameter (the standard deviation of the Heywood diameters/the arithmetic average value of the Heywood diameter×100).

When the coefficient of variation is small, the coefficient of variation indicates that the particle size distribution of the number distribution is sharp and the variation of the sizes of the particles is small.

(Range of Minor Axes)

The minor axes of the primary particles of the zinc oxide particles of the present invention are preferably 35 nm or more and 350 nm or less. The minor axes are more preferably 40 nm or more and still more preferably 45 nm or more. The minor axes are more preferably 330 nm or less and still more preferably 310 nm or less. Specifically, the minor axes are preferably 40 nm or more and 330 nm or less and more preferably 45 nm or more and 310 nm or less.

When the minor axes of the primary particles of the zinc oxide particles are within the above-described range, it is possible to obtain zinc oxide powder which is excellent in terms of storage stability and transparency and has a broad ultraviolet-shielding region and a low photocatalytic activity.

(Ranges of Heywood Diameters and Coefficient of Variation)

The Heywood diameters of the primary particles of the zinc oxide particles of the present invention are preferably 35 nm or more and 400 nm or less. The Heywood diameters are more preferably 40 nm or more and still more preferably 50 nm or more. The Heywood diameters are more preferably 390 nm or less and still more preferably 370 nm or less. Specifically, the Heywood diameters are preferably 40 nm or more and 390 nm or less and preferably 50 nm or more and 370 nm or less.

When the Heywood diameters of the primary particles are within the above-described range, it is possible to obtain zinc oxide powder which is excellent in terms of storage stability and transparency and has a broad ultraviolet-shielding region and a low photocatalytic activity.

In the present invention, the average value of the Heywood diameters can be arbitrarily selected depending on the necessity. For example, the average value may be 100 nm to 400 nm or 200 nm to 300 nm. When the average value is within the above-described range, effects of excellent UVA-shielding properties and good feelings to skin can be obtained.

The coefficient of variation of the number distribution of the Heywood diameters of the primary particles of the zinc oxide particles of the present invention is preferably 50% or less. The coefficient of variation is more preferably 45% or less and still more preferably 40% or less. In addition, the lower limit value of the coefficient of variation is not particularly limited as long as desired effects are obtained. The coefficient of variation may be 0.1% or more, 1% or more, 10% or more, or 15% or more depending on the necessity.

When the coefficient of variation in the number distribution of the Heywood diameters of the primary particles is within the above-described range, it is possible to obtain zinc oxide powder which is excellent in terms of storage stability and transparency and has a broad ultraviolet-shielding region and a low photocatalytic activity.

(Characteristics of Zinc Oxide Powder)

When the minor axes of the primary particles of the zinc oxide particles, the Heywood diameters of the primary particles, and the coefficient of variation of the number distribution are adjusted to the above-described range, it is possible to obtain zinc oxide powder which is excellent in terms of storage stability and transparency and has a broad ultraviolet-shielding region and a low photocatalytic activity. The reasons therefor can be considered as described below.

When the minor axes of the primary particles of all of the zinc oxide particles included in the zinc oxide powder and the Heywood diameters of the primary particles are set to 35 nm or more, the zinc oxide powder of the present invention does not include zinc oxide fine particles having portions with diameters of less than 35 nm (the minor axis and the Heywood diameter). All of the particles included in the zinc oxide powder have a minor axis of 35 nm or more and a Heywood diameter of 35 nm or more.

Therefore, under the above-described conditions, since there are no or a small number of small particles, fusion between particles caused by small particles during storage is suppressed, and thus it is possible to suppress changes in the specific surface area. In addition, since the zinc oxide powder does not include small particles, the specific surface area decreases, and the photocatalytic activity of the zinc oxide powder can be decreased. Meanwhile, even in a case in which particles not satisfying the above-described conditions are included, the number thereof is extremely small, and thus it is possible to obtain the above-described effects to a certain extent.

Meanwhile, when the minor axes of the primary particles of the zinc oxide particles are set to 350 nm or less, and the Heywood diameters of the primary particles of the zinc oxide particles are set to 400 nm or less, the zinc oxide powder of the present invention does not include coarse particles of zinc oxide. Therefore, zinc oxide powder having excellent transparency can be obtained.

In addition, when the minor axes of the primary particles of the zinc oxide particles, the Heywood diameters of the primary particles, and the coefficient of variation of the number distribution of the Heywood diameters of the primary particles are adjusted to the above-described ranges, particles having an excellent short-wavelength ultraviolet ray (UVB)-shielding properties and particles having an excellent long-wavelength ultraviolet ray (UVA)-shielding properties coexist in a mixed form in certain ranges. Therefore, wavelength ranges in which ultraviolet rays can be shielded become broad, and thus ultraviolet-shielding regions become broad. Meanwhile, the particles having an excellent short-wavelength ultraviolet ray (UVB)-shielding properties are considered as particles having excellent properties of shielding ultraviolet rays of, for example, 315 nm to 280 nm, and the particles having an excellent long-wavelength ultraviolet ray (UVA)-shielding properties are considered as particles having excellent properties of shielding ultraviolet rays of 400 nm to 315 nm, particularly, 400 nm to 370 nm.

(Ratio in Powder)

In the zinc oxide powder of the present invention, the content of zinc oxide particles in which the minor axes of the primary particles are 35 nm or more and 350 nm or less and the Heywood diameters of the primary particles are 35 nm or more and 400 nm or less is preferably 95% or more, more preferably 96% or more, still more preferably 98% or more, and most preferably 100% in the number distribution.

When the content of zinc oxide particles in which the minor axes of the primary particles are 35 nm or more and 350 nm or less and the Heywood diameters of the primary particles are 35 nm or more and 400 nm or less is within the above-described range, it is possible to obtain zinc oxide powder which is excellent in terms of storage stability and transparency and has a broad ultraviolet-shielding region.

Meanwhile, in what range the minor axes or Heywood diameters of the primary particles of the zinc oxide particles are present in the number distribution can be confirmed by means of the above-described analysis.

(Range of Major Axes)

The major axes of the primary particles of the zinc oxide particles are preferably 50 nm or more and 650 nm or less. The major axes are more preferably 60 nm or more and still more preferably 65 nm or more. The major axes are more preferably 600 nm or less and more preferably 580 nm or less. Specifically, the major axes are more preferably 60 nm or more and 600 nm or less and still more preferably 65 nm or more and 580 nm or less.

When the major axes of the primary particles of the zinc oxide particles are within the above-described range, it is possible to obtain zinc oxide powder which is excellent in terms of transparency and has a broad ultraviolet-shielding region. In addition, zinc oxide powder having an excellent degree of whiteness can be obtained.

(Range of Aspect Ratios)

The aspect ratios of the primary particles of the zinc oxide particles are preferably 1.0 or more and 4.0 or less. The aspect ratios are more preferably 3.8 or less and more preferably 3.5 or less. The aspect ratios are preferably 1.0 or more and also preferably 1.0. Specifically, the aspect ratios are more preferably 1.0 or more and 3.5 or less.

When the aspect ratios of the primary particles of the zinc oxide particles are within the above-described range, it is possible to obtain zinc oxide powder which is excellent in terms of storage stability and transparency and has a broad ultraviolet-shielding region.

(Fraction of Specific Particles in Zinc Oxide Particles)

For the zinc oxide powder of the present invention, the fraction of the zinc oxide particles in which the minor axes of the primary particles are 35 nm or more and 100 nm or less can be arbitrarily selected. The content of the zinc oxide particles in which the minor axes of the primary particles are 35 nm or more and 100 nm or less is preferably 1.5% or more and 10% or less, more preferably 2.0% or more and 9.5% or less, and still more preferably 2.0% or more and 9.0% or less in the minor axis-based number distribution of the primary particles.

When the minor axes of the primary particles of the zinc oxide particles are adjusted to the above-described range, zinc oxide powder having excellent storage stability and a broad ultraviolet-shielding region can be obtained. In addition, zinc oxide powder having a suppressed photocatalytic activity can be obtained.

For the zinc oxide powder of the present invention, the fraction of the zinc oxide particles in which the minor axes of the primary particles are more than 100 nm and 350 nm or less can be arbitrarily selected. The content of the zinc oxide particles in which the minor axes of the primary particles are more than 100 nm and 350 nm or less is preferably more than 90% and 98.5% or less and more preferably 91% or more and 98% or less in the minor axis-based number distribution of the primary particles.

When the minor axes of the primary particles of the zinc oxide particles are adjusted to the above-described range, zinc oxide powder having excellent storage stability and a broad ultraviolet-shielding region can be obtained.

(Specific Surface Area)

In the zinc oxide powder of the present invention, when the change ratio of the specific surface area which is obtained after being left to stand at a temperature of 150° C. and a relative humidity of 100% for 24 hours to the specific surface area which is obtained before being left to stand (the specific surface area after being left to stand to the specific surface area before being left to stand) is 0.9 or more and 1.1 or less, the storage stability may be considered to be excellent. The change ratio of the specific surface area is more preferably 0.95 or more and 1.05 or less.

In addition, in the zinc oxide powder of the present invention, the specific surface areas which are obtained before and after being left to stand at a temperature of 150° C. and a relative humidity of 100% for 24 hours are preferably 1.5 $m^2/g$ or more and 8.0 $m^2/g$ or less, more preferably 2.0 $m^2/g$ or more and 7.5 $m^2/g$ or less, and still more preferably 3.0 $m^2/g$ or more and 7.0 $m^2/g$ or less, respectively.

That is, in the zinc oxide powder of the present invention, the change ratio between the specific surface areas which are obtained before and after being left to stand under the above-described conditions is preferably 10% or less, more preferably 7% or less, and still more preferably 5% or less.

Leaving the zinc oxide powder to stand under high-temperature and high-humidity conditions serves as an ordinary storage acceleration test. Therefore, zinc oxide powder having a small change ratio of the specific surface area under the above-described conditions means that the change in the specific surface area is suppressed even in ordinary storage.

The above-described temperature and humidity conditions can be adjusted using, for example, a pressure cooker apparatus (a highly accelerated stress test system manufactured by ESPEC Corp., EHS-411M).

When the zinc oxide powder of the present invention is compared before and after the zinc oxide powder is left to stand at a temperature of 150° C. and a relative humidity of 100% for 24 hours, the change ratio of the specific surface area is small. That is, the zinc oxide powder of the present embodiment has performance that rarely changes even after the storage of the zinc oxide powder and thus has excellent storage stability.

When the specific surface area of the zinc oxide powder changes, the oil absorption amount of the zinc oxide powder changes. Therefore, dispersions or cosmetics prepared using zinc oxide powder having a changed specific surface area have a viscosity or senses such as skin feelings that change more than those of dispersions or cosmetics prepared using the zinc oxide powder having the original specific surface area. As described above, dispersions or cosmetics prepared using zinc oxide powder having a specific surface area that has changed during storage are not excellent in terms of quality stability.

In contrast, the zinc oxide powder of the present invention has a small change ratio of the specific surface area as described above. Therefore, the storage stability is excellent.

Therefore, in dispersions or cosmetics prepared using the zinc oxide powder of the present invention, changes in the viscosity, senses, and the like are suppressed, and thus the quality stability is excellent.

In the zinc oxide powder of the present invention, the specific surface areas can be measured using an ordinary method that is used in this field and may refer to, for example, values measured from nitrogen adsorption isothermal lines obtained by BET multipoint methods using an automatic specific surface area measurement instrument (trade name: BELSORP-Mini II, manufactured by MicrotracBEL Corp.).

(Evaluation of Photocatalytic Activity)

In the zinc oxide powder of the present invention, the decomposition rate of Brilliant Blue that is generated by the photocatalytic activity of the powder is preferably 70% or less. The reason therefor indicates that, when the decomposition rate of Brilliant Blue is 70% or less, the photocatalytic activity of the zinc oxide particles is suppressed. Therefore, the reactions of the above-described zinc oxide powder with other materials that are used for cosmetics or the like are suppressed, and consequently, the storage stability of cosmetic products can be enhanced.

The decomposition rate of Brilliant Blue is more preferably 60% or less and still more preferably 50% or less.

Here, the reasons for measuring the photocatalytic activity using Brilliant Blue are as described below.

Brilliant Blue is generally used as a coloring pigment for cosmetics as "Blue 1". In addition, Brilliant Blue has a relatively excellent stability to light, and thus the maximum value of absorbed wavelengths is near 630 nm. Therefore, Brilliant Blue absorbs ultraviolet light relatively weakly and is affected only to a small extent by light decomposition by ultraviolet rays. Furthermore, when compared with other colorants such as methylene blue, Brilliant Blue is not easily adsorbed to the surface of the zinc oxide powder. For the above-described reasons, Brilliant Blue is suitable for the evaluation of changes in the properties of colorants which are caused by the photocatalytic activity of the zinc oxide powder. Therefore, the photocatalytic activity was measured using Brilliant Blue.

The method for measuring the decomposition rate of Brilliant Blue is as described below.

First, a Brilliant Blue aqueous solution in which the content rate of Brilliant Blue is adjusted to a predetermined value (for example, 5 ppm) is produced. In addition, a predetermined amount (for example, 3 mL) is sampled from the Brilliant Blue aqueous solution onto a quartz cell. In addition, the zinc oxide powder is injected into this sampled Brilliant Blue aqueous solution so that the amount of the zinc oxide powder in the Brilliant Blue aqueous solution reaches 0.01% by mass and is ultrasonic-dispersed, thereby preparing a suspension. Next, this suspension is irradiated with ultraviolet rays having a predetermined wavelength from a predetermined distance (for example, 10 cm) for a predetermined time (for example, 10 minutes).

As an ultraviolet radiation lamp, it is possible to use, for example, a germicidal lamp GL20 (wavelength: 253.7 nm, ultraviolet output: 7.5 W, manufactured by Toshiba Corporation).

Next, supernatant liquid is sampled from this suspension irradiated with ultraviolet rays. The respective absorption spectra of the Brilliant Blue aqueous solution into which the zinc oxide powder is yet to be injected and the sampled supernatant liquid are measured using a spectrometer (manufactured by Shimadzu Corporation, Serial No.: UV-3150). In addition, the decomposition rate D of Brilliant Blue is computed from Expression (1) below using these measurement values.

$$D=(A0-A1)/A0 \qquad (1)$$

(Here, A0 represents the absorbance at the absorption maximum wavelength (near 630 nm) of the absorption spectrum of the Brilliant Blue aqueous solution (5 ppm), and A1 represents the absorbance at the absorption maximum wavelength of the absorption spectrum of the supernatant liquid.)

(Method for Manufacturing Zinc Oxide Powder)

Examples of the method for adjusting the minor axes, Heywood diameters, major axes, and aspect ratios of the primary particles of the zinc oxide particles in the zinc oxide powder to the ranges of the present invention include a method in which the production conditions of manufacturing methods being used are adjusted so that the sizes of the primary particles of the zinc oxide powder becomes uniform. For example, in a case in which the zinc oxide powder is produced using a thermal decomposition method, a method in which the heating variation is reduced by, during heating, slowing the temperature-increase rate, reducing the amount of zinc oxide powder being produced with a single round of the process, or the like is used. In addition, in a case in which the zinc oxide powder is produced using a gas-phase method, for example, a method in which the cooling variation is reduced by, during cooling that is carried out after a reaction at a high temperature, slowly cooling the components, reducing the amount of zinc oxide powder being produced with a single round of the process, or the like is used.

Examples of the method for manufacturing the zinc oxide powder of the present invention include the following method.

The fine particles of zinc oxide in which the specific surface area is 8 $m^2/g$ or more and 65 $m^2/g$ or less, the conductivity is 150 µS/cm or less, and the bulk specific volume is 1 mL/g or more and 10 mL/g or less are prepared as a raw material, and the fine particles are caused to further grow by means of heating or the like. Regarding the heating temperature and the heating time, different conditions may be selected depending on the amount and the like of the fine particles of the zinc oxide being heated. That is, the heating temperature and the heating time may be appropriately adjusted so that desired minor axes and Heywood diameters can be obtained depending on the amount of zinc oxide powder to be produced.

In a case in which the fine particles of zinc oxide as described above are used, the conductivity of the fine particles of zinc oxide is low, and thus the amount of impurities included in the zinc oxide fine particles is small, and the grains can be caused to uniformly grow without impairing the sintering of the fine particles of zinc oxide.

Therefore, it is possible to obtain zinc oxide powder having a coefficient of variation of 50% or less as described above.

The conductivity of the fine particles of the zinc oxide of the present invention which can be used in the method for manufacturing the zinc oxide powder of the present invention is preferably 150 µS/cm or less, more preferably 100 µS/cm or less, still more preferably 50 µS/cm or less, far still more preferably 30 µS/cm or less, and most preferably 10 µS/cm or less.

When the conductivity of the fine particles of the zinc oxide is within the above-described range, the above-described effects can be obtained.

The conductivity of the fine particles of zinc oxide refers to a value measured using the following method.

The fine particles of zinc oxide (10 g) and pure water (75 g) are mixed together, and this liquid mixture is put into a container and boiled on a hot plate for 10 minutes.

Next, the liquid mixture is cooled to room temperature in the air, and then pure water is added to the liquid mixture so that the total amount of the fine particles of zinc oxide and pure water reaches 85 g.

Next, the liquid mixture is separated into solid and liquid through centrifugal separation, and the conductivity of the supernatant liquid is measured using a conductivity meter (trade name: ES-12, manufactured by Horiba, Ltd.).

Examples of the method for adjusting the conductivity of the fine particles of zinc oxide to the above-described range include a method for decreasing the content of impurities in the fine particles of zinc oxide. Specifically, in a case in which the fine particles of zinc oxide are produced, fine particles of zinc oxide having a low conductivity can be obtained by using a highly-pure raw material, preventing the interfusion of impurities in the production step, providing an appropriate cleaning step in the process of the production step, or the like.

In the manufacturing method, the reason for the fine particles of zinc oxide having a specific surface area of 8 $m^2/g$ or more and 65 $m^2/g$ or less being preferably used is that the zinc oxide powder of the present invention can be obtained by causing the fine particles of zinc oxide having a specific surface area in this range to slowly grow.

The specific surface area of the fine particles of zinc oxide is more preferably 15 $m^2/g$ or more and 60 $m^2/g$ or less, still more preferably 20 $m^2/g$ or more and 50 $m^2/g$ or less, and particularly preferably 25 $m^2/g$ or more and 45 $m^2/g$ or less.

The reason for the fine particles of zinc oxide having a bulk specific volume of 1 mL/g to 10 mL/g being preferably used is that the zinc oxide powder of the present invention can be obtained by causing the fine particles of zinc oxide having a bulk specific volume in this range to slowly grow.

The bulk specific volume of the fine particles of zinc oxide is more preferably 1.5 mL/g or more and 9.5 mL/g or less, still more preferably 3.0 mL/g or more and 8.0 mL/g or less, and particularly preferably 4.0 mL/g or more and 7.0 mL/g or less.

The method for controlling the bulk specific volume of the fine particles of zinc oxide in the above-described range is not particularly limited, and a variety of methods can be selected. For example, in a case in which the fine particles of zinc oxide are produced using a thermal decomposition method as described in Japanese Laid-open Patent Publication No. 60-255620, the bulk specific volume of the zinc oxide powder can be controlled in the above-described range by adjusting the bulk specific volume of raw materials, adjusting the thermal decomposition temperature, carrying out crushing, or the like.

In addition, in a case in which the fine particles of zinc oxide are produced using a gas-phase method as described in Japanese Laid-open Patent Publication No. 63-288914, the bulk specific volume of the fine particles of zinc oxide can be controlled in the above-described range by appropriately adjusting temperatures in production processes.

The method for manufacturing the fine particles of zinc oxide which can be preferably used in the method for manufacturing the zinc oxide powder and in which the specific surface area is 8 $m^2/g$ or more and 65 $m^2/g$ or less, the conductivity is 150 pS/cm or less, and the bulk specific volume is 1 mL/g or more and 10 mL/g or less is not particularly limited. The method for manufacturing the fine particles of zinc oxide as described above may preferably include the above-described method for adjusting the specific surface area of the fine particles of zinc oxide, the method for adjusting the conductivity of the fine particles of zinc oxide, the method for adjusting the bulk specific volume of the fine particles of zinc oxide, and the like. Examples thereof include a method in which the above-described adjustment methods are appropriately carried out.

[Surface-Treated Zinc Oxide Powder]

For the zinc oxide powder of the present invention or zinc oxide particles included in the powder, at least some of the surface thereof may be treated with at least one of an inorganic component and an organic component. The zinc oxide powder or the particles which are surface-treated with at least one of an inorganic component and an organic component as described above are referred to as surface-treated zinc oxide powder or surface-treated zinc oxide particles.

The inorganic component and the organic component are appropriately selected depending on the applications of the zinc oxide powder.

In a case in which the surface-treated zinc oxide powder of the present invention is used for cosmetics, the inorganic component and the organic component are not particularly limited, and it is possible to use, for example, surface treatment agents that are generally used for cosmetics.

The inorganic component is, for example, at least one component selected from the group consisting of silica, alumina, and the like.

The organic component is, for example, at least one component selected from the group consisting of a silicone compound, an organopolysiloxane, a fatty acid, a fatty acid soap, a fatty acid ester, and an organic titanate compound.

In addition, a surfactant may be used as the inorganic component or the organic component.

In a case in which the zinc oxide powder or the particles are surface-treated with at least one of the inorganic component and the organic component, it is possible to suppress the photocatalytic activity of zinc oxide or improve the dispersibility of the zinc oxide powder in dispersion media.

The silicone compound that is used in the surface treatment can be arbitrarily selected. Examples of the silicone compound used in the surface treatment include silicone oil such as methyl hydrogen polysiloxane, dimethylpolysiloxane, and methyl phenyl polysiloxane; alkylsilane such as methyl trimethoxysilane, ethyl trimethoxysilane, hexyl trimethoxysilane, octyl trimethoxysilane, and octyl triethoxysilane; fluoroalkyl silane such as trifluoro methyl ethyl trimethoxysilane and heptadecafluorodecyl trimethoxysilane, methicone, hydrogen dimethicone, triethoxysilylethyl polydimethylsiloxyethyl dimethicone, triethoxysilylethylpolydimethylsiloxyethylhexyl dimethicone, (acrylate/tridecylacrylate/triethoxysilylpropyl methacrylate/dimethicone methacrylate) copolymers, triethoxycaprylylsilane, and the like.

These silicone compounds may be used singly or two or more silicone compounds may be used in combination.

In addition, as the silicone compound, copolymers of these silicone compounds may also be used.

Examples of the fatty acid include palmitic acid, isooctadecanoic acid, stearic acid, lauric acid, myristic acid, behenic acid, oleic acid, rosin acid, 12-hydroxystearic acid, polyhydroxystearic acid, and the like.

Examples of the fatty acid soap include aluminum stearate, calcium stearate, aluminum 12-hydroxystearate, and the like.

Examples of the fatty acid ester include dextrin fatty acid esters, cholesterol fatty acid esters, sucrose fatty acid esters, starch fatty acid esters, and the like.

Examples of the organic titanate compound include isopropyl triisostearoyl titanate, isopropyl dimethacryl isostearoyl titanate, isopropyl tri(dodecyl) benzene sulfonyl titanate, neopentyl (diallyl)oxy tri(dioctyl) phosphate titanate, neopentyl (diallyl)oxy trineododecanoyl titanate, and the like.

These compounds may be used singly or two or more compounds may be used in combination.

In a case in which the surface-treated zinc oxide powder of the present invention is used for industrial applications of ultraviolet-shielding films or gas barrier films, in addition to the inorganic component or the organic component used for cosmetics, ordinary dispersants which are used to disperse particles such as an anionic dispersant, a cationic dispersant, a nonionic dispersant, a silane coupling agent, or a wetting dispersant can be appropriately selected and used.

In a case in which the above-described surface treatment is carried out, it is possible to suppress the photocatalytic activity of zinc oxide or improve the dispersibility of the zinc oxide powder in dispersion media.

The method for manufacturing the surface-treated zinc oxide powder of the present invention is not particularly limited. In a case in which the surface treatment is carried out, well-known methods may be appropriately carried out depending on the components used in the surface treatment.

[Dispersion]

A dispersion of the present invention contains the zinc oxide powder of the present invention and a dispersion medium.

Meanwhile, a paste-form dispersion element having a high viscosity is also included in the scope of the dispersion of the present invention in terms of the meaning.

The content of the zinc oxide powder in the dispersion of the present invention is not particularly limited and may be appropriately adjusted depending on desired characteristics.

In a case in which the dispersion of the present invention is used for cosmetics, the content of the zinc oxide powder in the dispersion can be arbitrarily selected. For example, the content may be 10% by mass or more and 90% by mass or less and is preferably 30% by mass or more and 90% by mass or less, more preferably 40% by mass or more and 85% by mass or less, and still more preferably 50% by mass or more and 80% by mass or less.

When the content of the zinc oxide powder in the dispersion is, for example, 30% by mass or more and 90% by mass or less, the dispersion contains a high concentration of the zinc oxide powder, and thus it is possible to improve the degree of freedom in formulations and maintain the viscosity of the dispersion at which the dispersion can be easily handled.

The viscosity of the dispersion of the present invention can be arbitrarily selected. For example, the viscosity is preferably 5 Pa·s or more and 300 Pa·s or less, more preferably 8 Pa·s or more and 100 Pa·s or less, still more preferably 10 Pa·s or more and 80 Pa·s or less, and most preferably 15 Pa·s or more and 60 Pa·s or less.

When the viscosity of the dispersion is within the above-described range, it is possible to obtain dispersions that can be easily handled even when, for example, including a high concentration of the solid content (zinc oxide powder).

The dispersion medium is appropriately selected depending on the application of the dispersion. Examples of preferred dispersion media will be described below, but the dispersion medium in the dispersion of the present invention is not limited thereto.

As the dispersion medium, for example, water, alcohols such as methanol, ethanol, 1-propanol, 2-propanol, 1-butanol, 2-butanol, octanol, and glycerin; esters such as ethyl acetate, butyl acetate, ethyl lactate, propylene glycol monomethyl ether acetate, and γ-butyrolactone; and ether such as diethyl ether, ethylene glycol monomethyl ether (methyl cellosolve), ethylene glycol monoethyl ether (ethyl cellosolve), ethylene glycol monobutyl ether (butyl cellosolve), diethylene glycol monomethyl ether, and diethylene glycol monoethyl ether can be used.

These dispersion media may be used singly or a mixture of two or more dispersion media may be used.

In addition, examples of other dispersion media that can be used include ketones such as acetone, methyl ethyl ketone, methyl isobutyl ketone, acetyl acetone, and cyclohexanone; aromatic hydrocarbons such as benzene, toluene, xylene, and ethyl benzene; cyclic hydrocarbon such as cyclohexane; amides such as dimethylformamide, N,N-dimethylacetoacetamide, and N-methylpyrrolidone; chain-like polysiloxanes such as dimethyl polysiloxane, methyl phenyl polysiloxane, and diphenyl polysiloxane; and the like.

These dispersion media may be used singly or a mixture of two or more dispersion media may be used.

In addition, examples of additional dispersion medium include cyclic polysiloxanes such as octamethyl cyclotetrasiloxane, decamethyl cyclopentasiloxane, and dodecamethyl cyclohexasiloxane; and denatured polysiloxanes such as amino-denatured polysiloxane, polyether-denatured polysilocane, alkyl-denatured polysiloxane, fluorine-denatured polysiloxane, and the like.

These dispersion media may be used singly or a mixture of two or more dispersion media may be used.

Examples of dispersion media other than the above-described dispersion media also include hydrophobic dispersion media such as hydrocarbon oils such as liquid paraffin, squalane, isoparaffin, branched chain-like light paraffin, petrolatum, and ceresin, ester oils such as isopropyl myristate, cetyl isooctanoate, and glyceryl trioctanoate, silicone oils such as decamethyl cyclopentasiloxane, dimethyl polysiloxane, and methyl phenyl polysiloxane, higher fatty acids such as lauric acid, myristic acid, palmitic acid, and stearic acid, and higher alcohols such as lauryl alcohol, cetyl alcohol, stearyl alcohol, hexyl dodecanol, and isostearyl alcohol.

The amount of the dispersion medium in the dispersion can be arbitrarily selected depending on the necessity. Examples of the amount thereof include 10% to 90% by mass, 10% to 70% by mass, 15% to 60% by mass, 20% to 50% by mass, and the like, but the amount thereof is not limited thereto.

The dispersion of the present invention may include ordinarily-used additives as long as the characteristics thereof are not impaired.

Examples of the additives include dispersants, stabilizers, water-soluble binders, viscosity improvers, oil-soluble preservatives, ultraviolent absorbers, oil-soluble chemicals, oil-soluble pigments, oil-soluble proteins, plant oils, animal oils, and the like. The amount thereof may be arbitrarily selected depending on the necessity.

The method for manufacturing the dispersion of the present invention is not particularly limited. Examples thereof include a method in which the zinc oxide powder of the present invention and a dispersion medium are mechanically dispersed using a well-known dispersion apparatus, and the like.

A dispersion apparatus can be arbitrarily selected, and examples thereof include a stirrer, a planetary mixer, a homogenizer, an ultrasonic homogenizer, a sand mill, a ball mill, a roll mill, and the like.

The dispersion of the present invention can be used for compositions and the like having an ultraviolet-shielding function, a gas transmission-suppressing function, and the like in addition to cosmetics.

[Composition]

A composition of the present invention includes the zinc oxide powder of the present invention, a resin, and a dispersion medium.

The content of the zinc oxide powder in the composition of the present invention may be appropriately adjusted depending on desired characteristics. For example, the content thereof may be 3% by mass or more and 80% by mass, or be 5% by mass or more and 60% by mass or less, and is preferably 10% by mass or more and 40% by mass or less and more preferably 20% by mass or more and 30% by mass or less.

When the content of the zinc oxide powder in the composition is, for example, 10% by mass or more and 40% by mass or less, the composition includes a high concentration of the solid content (zinc oxide powder), and thus the characteristics (ultraviolet-shielding properties and the like) of zinc oxide are sufficiently obtained, and it is possible to obtain compositions in which the zinc oxide powder is uniformly dispersed.

The dispersion medium is not particularly limited as long as the dispersion medium is ordinarily used for industrial applications. Examples thereof include water, alcohols such as methanol, ethanol, and propanol, methyl acetate, ethyl acetate, toluene, methyl ethyl ketone, methyl isobutyl ketone, and the like. The dispersion medium exemplified in the section of the dispersion may also be used.

The content of the dispersion medium in the composition of the present invention is not particularly limited and may be appropriately adjusted depending on the intended characteristics of the composition. For example, the content thereof is, for example, 5% to 95% by mass, 2% to 50% by mass, or 40% to 85% by mass. However, the content thereof is not limited thereto.

The resin can be used without any particular limitations as long as the resin is generally used for industrial applications, and examples thereof include an acrylic resin, an epoxy resin, a urethane resin, a polyester resin, a silicone resin, and the like.

The content of the resin in the composition of the present invention is not particularly limited and may be appropriately adjusted depending on the intended characteristics of the composition. For example, the content thereof is 1% to 80% by mass, 2% to 50% by mass, 5% to 20% by mass, or the like. However, the content thereof is not limited thereto.

The composition of the present invention may include ordinarily-used additives as long as the characteristics thereof are not impaired.

Examples of the additives include polymerization initiators, dispersants, preservatives, and the like.

The method for manufacturing the composition of the present invention is not particularly limited. Examples thereof include a method in which the zinc oxide powder of the present invention, the resin, and the dispersion medium are mechanically mixed together using a well-known mixing apparatus.

In addition, there is another method in which the above-described dispersion and the resin are mechanically mixed together using a well-known mixing apparatus.

Examples of the mixing apparatus include a stirrer, a planetary mixer, an ultrasonic homogenizer, and the like.

The composition of the present invention can be used for a variety of applications depending on the necessity. For example, when the composition of the present invention is applied to a plastic base material such as a polyester film using an ordinary application method such as a roll coating method, a flow coating method, a spray coating method, a screen printing method, a brush coating method, or an immersion method, it is possible to form coated films. The coated films can be used as ultraviolet-shielding films or gas barrier films.

[Cosmetic]

A cosmetic of the present invention includes at least one of the zinc oxide powder of the present invention and the dispersion of the present invention. That is, the cosmetic may include either or both the zinc oxide powder and the dispersion.

The cosmetic of the present invention preferably further includes cosmetic product base raw materials.

Here, the cosmetic product base raw materials refer to various raw materials that form the main body of cosmetic products and can be arbitrarily selected. Examples thereof include oily raw materials, aqueous raw materials, surfactants, powder raw materials, and the like. These raw materials may be used singly or two or more raw materials may be used in combination. Examples of the oily raw material include oils and fats, higher aliphatic acids, higher alcohols, ester oils, and the like.

Examples of the aqueous raw materials include purified water, alcohols, viscosity improvers, and the like.

Examples of the powder raw material include colored pigments, white pigments, pearl agents, extender pigments, and the like.

The cosmetic of the present invention can be obtained by, for example, blending the dispersion of the present invention into the cosmetic product base raw materials such as emulsions, cream, foundation, lip sticks, blushes, or eye shadows as in the related art.

In addition, it is also possible to blend the cosmetic of the present invention, for example, the zinc oxide powder of the present invention into oil phases or water phases so as to produce O/W-type or W/O-type emulsions and then blend the emulsions with the cosmetic product base raw materials.

The content of the zinc oxide powder in the cosmetic may be appropriately adjusted depending on desired characteristics. For example, the lower limit of the content of the zinc oxide powder may be 0.01% by mass or more, 0.1% by mass or more, or 1% by mass or more. In addition, the upper limit of the content of the zinc oxide powder may be 50% by mass or less, 40% by mass or less, or 30% by mass or less.

Hereinafter, a sunscreen cosmetic, which is an example of the cosmetic, will be specifically described.

In order to effectively shield ultraviolet rays, particularly, long-wavelength ultraviolet rays (UVA), the lower limit of the content of the zinc oxide powder in the sunscreen cosmetic can be arbitrarily selected. The content of the zinc oxide powder is preferably 0.01% by mass or more, more preferably 0.1% by mass or more, and still more preferably 1% by mass or more.

In addition, the upper limit of the content of the zinc oxide powder in the sunscreen cosmetic can also be arbitrarily selected, may be 50% by mass or less, 40% by mass or less, or 30% by mass or less.

The sunscreen cosmetic may include a hydrophobic dispersion medium, inorganic fine particles or an inorganic pigment other than the zinc oxide powder, a hydrophilic dispersion medium, oil and fat, a surfactant, a moisturizing agent, a viscosity improver, a pH adjuster, a nutritional supplement, an antioxidant, a perfume, and the like depending on the necessity. The amount thereof can be arbitrarily selected depending on the necessity.

Examples of the hydrophobic dispersion medium include hydrocarbon oils such as such as liquid paraffin, squalane, isoparaffin, branched chain-like light paraffin, petrolatum, and ceresin, ester oils such as isopropyl myristate, cetyl isooctanoate, and glyceryl trioctanoate, silicone oils such as decamethyl cyclopentasiloxane, dimethyl polysiloxane, and methyl phenyl polysiloxane, higher fatty acids such as lauric acid, myristic acid, palmitic acid, and stearic acid, and higher alcohols such as lauryl alcohol, cetyl alcohol, stearyl alcohol, hexyl dodecanol, and isostearyl alcohol.

Examples of the inorganic fine particles or the inorganic pigment other than the zinc oxide powder include calcium carbonate, calcium phosphate (apatite), magnesium carbonate, calcium silicate, magnesium silicate, aluminum silicate, kaolin, talc, titanium oxide, aluminum oxide, yellow oxide of iron, γ-iron oxide, cobalt titanate, cobalt violet, silicon oxide, and the like.

The sunscreen cosmetic may further include at least one organic ultraviolet absorber. The cosmetic containing both the zinc oxide powder and the organic ultraviolet absorber is preferred since the cosmetic broadens the ultraviolet-shielding region through a booster effect. Examples of the organic ultraviolet absorber include a benzotriazole-based ultraviolet absorber, a benzoyl methane-based ultraviolet absorber, a benzoic acid-based ultraviolet absorber, an anthranilic acid-based ultraviolet absorber, a salicylic acid-based ultraviolet absorber, a cinnamic acid-based ultraviolet absorber, a silicone-based cinnamic acid ultraviolet absorber, organic ultraviolet absorbers other than the above-described ultraviolet absorbers, and the like.

Examples of the benzotriazole-based ultraviolet absorber include 2,2'-hydroxy-5-methylphenylbenzotriazole, 2-(2'-hydroxy-5'-t-octylphenyl) benzotriazole, 2-(2'-hydroxy-5'-methylphenyl)benzotriazole, and the like.

Examples of the benzoyl methane-based ultraviolet absorber include dibenzalazine, dianisoylmethane, 4-tert-butyl-4'-methoxydibenzoylmethane, 1-(4'-isopropylphenyl)-3-phenyl propane-1,3-dione, 5-(3,3'-dimethyl-2-norbornylidene)-3-pentane-2-one, and the like.

Examples of the benzoic acid-based ultraviolet absorber include para-aminobenzoic acid (PABA), PABA monoglycerin ester, N,N-dipropoxy PABA ethyl ester, N,N-diethoxy PABA ethyl ester, N,N-dimethyl PABA ethyl ester, N,N-dimethyl PABA butyl ester, N,N-dimethyl PABA methyl ester, and the like.

Examples of the anthranilic acid-based ultraviolet absorber include homo methyl-N-acetyl anthranilate and the like.

Examples of the salicylic acid-based ultraviolet absorber include amyl salicylate, methyl salicylate, homo menthyl salicylate, octyl salicylate, phenyl salicylate, benzyl salicylate, p-2-propnol phenyl salicylate, and the like.

Examples of the cinnamic acid-based ultraviolet absorber include octyl methoxycinnamate, di-para methoxy cinnamate-mono-2-glyceryl ethylhexanoate, octyl cinnamate, ethyl-4-isopropyl cinnamate, methyl-2,5-diisoprpyle cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate(2-ethylhexyl-p-methoxy cinnmate), 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, glyceryl mono-2-ethylhexanoyl-diparamethoxy cinnamate, and the like.

Examples of the silicone-based cinnamic acid ultraviolet absorber include
[3-bis(trimethylsiloxy)methylsilyl-1-methylpropyl]-3,4,5-trimethoxy cinnamate,
[3-bis(trimethylsiloxy)methylsilyl-3-methylpropyl]-3,4,5-trimethoxy cinnamate,
[3-bis(trimethylsiloxy)methylsilylpropyl]-3,4,5-trimethoxy cinnamate,
[3-bis(trimethylsiloxy)methylsilylbutyl]-3,4,5-trimethoxy cinnamate,
[3-tris(trimethylsiloxy)silylbutyl]-3,4,5-trimethoxy cinnamate,
[3-tris(trimethylsiloxy) silyl-1-methylpropyl]-3,4-dimethoxy cinnamate, and the like.

Examples of the organic ultraviolet absorbers other than the above-described ultraviolet absorbers include
3-(4'-methylbenzyliene)-d,l-camphor,
3-benzylidene-d,l-camphor, urocanic acid, ethyl urocanate esters, 2-phenyl-5-methylbenzoxane-2-one,
5-(3,3'-dimethyl-2-norbornylidene)-3-pentane-2-one, silicone-denatured ultraviolet absorbers, fluorine-denatured ultraviolet absorbers, and the like.

As described above, according to the zinc oxide powder of the present invention, the zinc oxide particles having a minor axis of the primary particle of 35 nm or more and 350 nm or less and having a Heywood diameter of the primary particle of 35 nm or more and 400 nm or less are included, and the coefficient of variation of the number distribution of the Heywood diameters is 50% or less. Therefore, it is possible to obtain zinc oxide powder which is excellent in terms of storage stability and transparency, is excellent in terms of, particularly, the stability of the specific surface area over time, and has a broad ultraviolet-shielding region.

In the surface-treated zinc oxide powder of the present invention, at least some of the surface of the zinc oxide powder of the present invention is preferably surface-treated with at least one of the inorganic component and the organic component. Therefore, it is possible to further suppress the photocatalytic activity of zinc oxide and improve the dispersibility in dispersion media.

The dispersion of the present invention contains the zinc oxide powder of the present invention, and thus dispersions having substantially the same properties as those before being stored regardless of the storage period of the zinc oxide powder can be obtained, and thus the quality stability is excellent.

In addition, in a case in which the viscosity of the dispersion of the present invention is 5 Pa·s or more and 300 Pa·s or less, the handling of the dispersion becomes easier.

The composition of the present invention contains the zinc oxide powder of the present invention, and thus compositions having substantially the same properties as those before being stored regardless of the storage period of the zinc oxide powder can be obtained, and thus the quality stability is excellent.

According to the cosmetic of the present invention, the cosmetic contains at least one selected from the zinc oxide powder of the present invention and the dispersion of the present invention, and thus cosmetics having substantially the same properties as those before being stored regardless of the storage period of the zinc oxide powder can be obtained, and thus the quality stability is excellent.

EXAMPLES

Hereinafter, the present invention will be more specifically described using examples and comparative examples, but the present invention is not limited to the following examples.

Example 1

"Production of Zinc Oxide Powder"

The fine particles of zinc oxide having a specific surface area of 26.2 m$^2$/g, a conductivity of 11.4 pS/cm, and a bulk specific volume of 5.8 mL/g were heated, thereby obtaining zinc oxide powder A1 of Example 1.

"Evaluation of Zinc Oxide Powder"

The zinc oxide powder A1 of Example 1 was observed using the following method. As a result, the zinc oxide powder was clarified as the following zinc oxide powder.

The minor axes of all of the observed primary particles of the zinc oxide powder A1 were in a range of 55 nm or more and 259 nm or less;

The Heywood diameters of all of the observed primary particles were in a range of 77 nm or more and 308 nm or less;

The coefficient of variation of the number distribution of the Heywood diameters of the primary particles was 26%;

The major axes of all of the observed primary particles were in a range of 92 nm or more and 436 nm or less;

The aspect ratios of all of the observed primary particles were in a range of 1.0 or more and 2.4 or less;

The content of zinc oxide particles in which the minor axes of the primary particles were 35 nm or more and 350 nm or less and the Heywood diameters of the primary particles were 35 nm or more and 400 nm or less was 100% in the number distribution; and The content rate of zinc oxide particles in which the minor axes of the primary particles were 35 nm or more and 100 nm or less was 8.9% in the number distribution.

The zinc oxide powder A1 of Example 1 was left to stand at a temperature of 150° C. and a relative humidity of 100% for 24 hours using a pressure cooker apparatus (a highly accelerated stress test system manufactured by ESPEC Corp., EHS-411M).

The specific surface area which is obtained before being left to stand was 4.7 m$^2$/g, the specific surface area which is obtained after being left to stand was 4.9 m$^2$/g, and the change ratio of the specific surface area which is obtained after being left to stand to the specific surface area which is obtained before being left to stand was 1.03 (4.9/4.7).

(Measurement of Minor Axes of Primary Particles of Zinc Oxide Particles, Major Axes of Primary Particles, Heywood Diameters of Primary Particles, and Aspect Ratios of Primary Particles)

The minor axes of the primary particles of the zinc oxide particles, the major axes of the primary particles, the Heywood diameters of the primary particles, and the aspect ratios of the primary particles were measured using the following method according to the method based on Japanese Industrial Standards JIS Z 8827-1:2008 "Particle size analysis Image analysis methods-Part 1: Static image analysis methods".

An electronic microscopic picture of 200 particles was captured using a field emission-type microscopic microscope (FE-SEM)S-4800 (manufactured by Hitachi High Technologies Corporation). Next, this electron microscopic picture was analyzed using image particle size distribution analysis software Mac-View Ver. 4 (manufactured by Mountech Co., Ltd.), and the minor axes of the primary particles, the major axes of the primary particles, the Heywood diameters of the primary particles, and the aspect ratios of the primary particles were determined.

(Measurement of Specific Surface Area of Zinc Oxide Powder)

The specific surface area of the zinc oxide powder was measured from nitrogen (N$_2$) adsorption isothermal lines obtained by BET multipoint methods using an automatic specific surface area measurement instrument (trade name: BELSORP-Mini II, manufactured by MicrotracBEL Corp.).

Example 2

"Production of Zinc Oxide Powder"

The fine particles of zinc oxide having a specific surface area of 28.9 m$^2$/g, a conductivity of 8.8 µS/cm, and a bulk specific volume of 6.2 mL/g were heated, thereby obtaining zinc oxide powder A2 of Example 2.

"Evaluation of Zinc Oxide Powder"

The zinc oxide powder A2 of Example 2 was observed using the same method as in Example 1. As a result, the zinc oxide powder was clarified as the following zinc oxide powder.

The minor axes of all of the primary particles of the observed zinc oxide particles were 67 nm or more and 298 nm or less;

The Heywood diameters of all of the observed primary particles were 148 nm or more and 360 nm or less;

The coefficient of variation of the number distribution of the Heywood diameters of the primary particles was 16%;

The major axes of all of the observed primary particles were in a range of 164 nm or more and 569 nm or less;

The aspect ratios of all of the observed primary particles were in a range of 1.0 or more and 3.2 or less;

The content of zinc oxide particles in which the minor axes of the primary particles were 35 nm or more and 350 nm or less and the Heywood diameters of the primary particles were 35 nm or more and 400 nm or less was 100% in the number distribution; and The content rate of zinc oxide particles in which the minor axes of the primary particles were 35 nm or more and 100 nm or less was 2.3% in the number distribution.

The zinc oxide powder A2 of Example 2 was left to stand at a temperature of 150° C. and a relative humidity of 100% for 24 hours using a pressure cooker apparatus.

In addition, the minor axes of the primary particles of the zinc oxide particles, the major axes of the primary particles, the Heywood diameters of the primary particles, and the aspect ratios of the primary particles were measured in the same manner as in Example 1.

In addition, the specific surface area of the zinc oxide powder was measured in the same manner as in Example 1. The specific surface area which is obtained before being left to stand was 3.9 m$^2$/g, the specific surface area which is obtained before being left to stand was 3.9 m$^2$/g, and the change ratio of the specific surface area which is obtained after being left to stand to the specific surface area which is obtained before being left to stand was 1.0 (3.9/3.9).

Example 3

"Production of Zinc Oxide Powder"

The fine particles of zinc oxide having a specific surface area of 29.7 m$^2$/g, a conductivity of 12.9 pS/cm, and a bulk specific volume of 5.5 mL/g were heated, thereby obtaining zinc oxide powder A3 of Example 3.

"Evaluation of Zinc Oxide Powder"

The zinc oxide powder A3 of Example 3 was observed using the same method as in Example 1. As a result, the zinc oxide powder was clarified as the following zinc oxide powder.

The minor axes of all of the primary particles of the observed zinc oxide particles were 55 nm or more and 302 nm or less;

The Heywood diameters of all of the observed primary particles were 61 nm or more and 302 nm or less;

The coefficient of variation of the number distribution of the Heywood diameters of the primary particles was 32%;

The major axes of all of the observed primary particles were in a range of 61 nm or more and 505 nm or less;

The aspect ratios of all of the observed primary particles were in a range of 1.0 or more and 3.2 or less;

The content of zinc oxide particles in which the minor axes of the primary particles were 35 nm or more and 350 nm or less and the Heywood diameters of the primary particles were 35 nm or more and 400 nm or less was 100% in the number distribution; and The content rate of zinc oxide particles in which the minor axes of the primary particles were 35 nm or more and 100 nm or less was 7.5% in the number distribution.

The zinc oxide powder A3 of Example 3 was left to stand at a temperature of 150° C. and a relative humidity of 100% for 24 hours using a pressure cooker apparatus.

In addition, the minor axes of the primary particles of the zinc oxide particles, the major axes of the primary particles, the Heywood diameters of the primary particles, and the aspect ratios of the primary particles were measured in the same manner as in Example 1.

In addition, the specific surface area of the zinc oxide powder was measured in the same manner as in Example 1. The specific surface area which is obtained before being left to stand was 5.1 m$^2$/g, the specific surface area which is obtained before being left to stand was 5.0 m$^2$/g, and the change ratio of the specific surface area which is obtained after being left to stand to the specific surface area which is obtained before being left to stand was 0.98 (5.0/5.1).

Comparative Example 1

Zinc oxide powder A4 (commercially available product) was prepared. This powder A4 was observed using the same method as in Example 1. As a result, the zinc oxide powder was clarified as the following zinc oxide powder.

The minor axes of all of the primary particles of the observed zinc oxide particles were 5 nm or more and 154 nm or less;
The Heywood diameters of all of the observed primary particles were 13 nm or more and 182 nm or less;
The coefficient of variation of the number distribution of the Heywood diameters of the primary particles was 66%;
The major axes of all of the observed primary particles were in a range of 19 nm or more and 259 nm or less;
The aspect ratios of all of the observed primary particles were in a range of 1.0 or more and 6.6 or less;
The content of zinc oxide particles in which the minor axes of the primary particles were 35 nm or more and 350 nm or less and the Heywood diameters of the primary particles were 35 nm or more and 400 nm or less was 34% in the number distribution;
The content rate of zinc oxide particles in which the minor axes of the primary particles were 35 nm or more and 100 nm or less was 34.3% in the number distribution;
The content rate of particles in which the minor axes of the primary particles were less than 35 nm was 64.0%.

The zinc oxide powder A4 (commercially available product) was left to stand at a temperature of 150° C. and a relative humidity of 100% for 24 hours using a pressure cooker apparatus.

As described above, the minor axes of the primary particles of the zinc oxide particles of Comparative Example 1, the major axes of the primary particles, the Heywood diameters of the primary particles, the aspect ratios of the primary particles, and the like were measured in the same manner as in Example 1.

The specific surface area of the zinc oxide powder was also measured in the same manner as in Example 1. The specific surface area which is obtained before being left to stand was 12.5 m$^2$/g, the specific surface area which is obtained before being left to stand was 8.8 m$^2$/g, and the change ratio of the specific surface area which is obtained after being left to stand to the specific surface area which is obtained before being left to stand was 0.70 (8.8/12.5).

Comparative Example 2

JIS 1-type zinc oxide powder was prepared. This powder was observed using the same method as in Example 1. As a result, the zinc oxide powder was clarified as the following zinc oxide powder.

The minor axes of all of the primary particles of the observed zinc oxide particles were 32 nm or more and 616 nm or less;
The Heywood diameters of all of the observed primary particles were 45 nm or more and 733 nm or less;
The coefficient of variation of the number distribution of the Heywood diameters of the primary particles was 58%;
The major axes of all of the observed primary particles were in a range of 54 nm or more and 871 nm or less;
The aspect ratios of all of the observed primary particles were in a range of 1.0 or more and 4.5 or less;
The content of zinc oxide particles in which the minor axes of the primary particles were 35 nm or more and 350 nm or less and the Heywood diameters of the primary particles were 35 nm or more and 400 nm or less was 92% in the number distribution;
The content rate of zinc oxide particles in which the minor axes of the primary particles were 35 nm or more and 100 nm or less was 28.3% in the number distribution;
The content rate of particles in which the minor axes of the primary particles were less than 35 nm was 2.7%.

The zinc oxide powder A5 was left to stand at a temperature of 150° C. and a relative humidity of 100% for 24 hours using a pressure cooker apparatus.

As described above, the minor axes of the primary particles of the zinc oxide particles of Comparative Example 2, the major axes of the primary particles, the Heywood diameters of the primary particles, the aspect ratios of the primary particles, and the like were measured in the same manner as in Example 1.

The specific surface area of the zinc oxide powder was also measured in the same manner as in Example 1. The specific surface area which is obtained before being left to stand was 3.7 m$^2$/g, the specific surface area which is obtained before being left to stand was 3.2 m$^2$/g, and the change ratio of the specific surface area which is obtained after being left to stand to the specific surface area which is obtained before being left to stand was 0.86 (3.2/3.7).

From the results of Examples 1 to 3 and Comparative Examples 1 and 2 shown in Table 1, it was confirmed that, in the zinc oxide powder which contained the zinc oxide particles in which the minor axes of the primary particles were 35 nm or more and 350 nm or less and the Heywood diameters of the primary particles were 35 nm or more and 400 nm or less and in which the coefficient of variation of the number distribution of the Heywood diameters was 50% or less, the change ratio of the specific surface area was small even when the zinc oxide powder was left to stand under conditions of high temperatures and high humidity, and the storage stability was excellent.

TABLE 1

|  | EXAMPLE 1 | EXAMPLE 2 | EXAMPLE 3 | COMPARATIVE EXAMPLE 1 | COMPARATIVE EXAMPLE 2 |
|---|---|---|---|---|---|
| Minor axes of primary particles (nm) | 55~259 | 67~298 | 55~302 | 5~154 | 32~616 |
| Heywood diameters of primary particles (nm) | 77~308 | 148~360 | 61~302 | 13~182 | 45~733 |

TABLE 1-continued

| | EXAMPLE 1 | EXAMPLE 2 | EXAMPLE 3 | COMPARATIVE EXAMPLE 1 | COMPARATIVE EXAMPLE 2 |
|---|---|---|---|---|---|
| Coefficient of variation of number distribution of Heywood diameters of primary particles (%) | 26 | 16 | 32 | 66 | 58 |
| Major axes of primary particles (nm) | 92~436 | 164~569 | 61~505 | 19~259 | 54~871 |
| Aspect ratios of primary particles | 1.0~2.4 | 1.0~3.2 | 1.0~3.2 | 1.0~6.6 | 1.0~4.5 |
| Fraction of zinc oxide particles in which minor axes of primary particles are 35 nm or more and 350 nm or less and Heywood diameter of primary particles are 35 nm or more and 400 nm or less in powder (%) | 100 | 100 | 100 | 49 | 92 |
| Content rate of particles in which minor axes of primary particles are less than 35 nm | 0 | 0 | 0 | 64.0 | 2.7 |
| Content rate of zinc oxide particles in which minor axes of primary particles are 35 nm or more and 100 nm or less in powder (%) | 8.9 | 2.3 | 7.5 | 34.3 | 28.3 |
| Specific surface area obtained before being left to stand ($m^2/g$) | 4.7 | 3.9 | 5.1 | 12.5 | 3.7 |
| Specific surface area obtained after being left to stand ($m^2/g$) | 4.9 | 3.9 | 5.0 | 8.8 | 3.2 |
| Change ratio of specific surface area | 1.03 | 1.00 | 0.98 | 0.70 | 0.86 |

"Evaluation of Photocatalytic Activity"

The photocatalytic activity of the zinc oxide powder of Examples 1 to 3 and Comparative Examples 1 and 2 was measured using the following method.

A Brilliant Blue aqueous solution in which the content rate of Brilliant Blue was adjusted to 5 ppm was produced, and 0.0003 g of each zinc oxide powder was injected into 3 g of the Brilliant Blue aqueous solution and was ultrasonic-dispersed, thereby adjusting a suspension. Next, this suspension was irradiated using an ultraviolet lamp (central wavelength: 254 nm) at an irradiation distance of 10 cm for 10 minutes, and then the supernatant liquid was sampled.

Next, the respective spectrophotometric spectra of the Brilliant Blue aqueous solution into which the zinc oxide was yet to be injected and the supernatant liquid were measured using a spectrometer (manufactured by Shimadzu Corporation, Serial No.: UV-3150). The decomposition rate D of Brilliant Blue was computed from Expression (1) using these measurement values.

As a result, the decomposition rates of Brilliant Blue were 49% in Example 1, 46% in Example 2, 55% in Example 3, 80% in Comparative Example 1, and 82% in Comparative Example 2.

That is, it was confirmed that the zinc oxide powder which contained the zinc oxide particles in which the minor axes of the primary particles were 35 nm or more and 350 nm or less and the Heywood diameters of the primary particles were 35 nm or more and 400 nm or less and in which the coefficient of variation of the number distribution of the Heywood diameters of the primary particles was 50% or less was also excellent in terms of the photocatalytic activity.

"Evaluation of Ultraviolet-Shielding Properties of Sunscreen Cream"

The zinc oxide powder of Examples 1 to 3 and Comparative Examples 1 and 2 was used, and components were blended according to the formulation shown in Table 2, thereby respectively formulating sunscreen creams B1 (Example 1), B2 (Example 2), B3 (Example 3), B4 (Comparative Example 1), and B5 (Comparative Example 2) for which the powder of Examples 1 to 3 and Comparative Examples 1 and 2 was used.

TABLE 2

| Components | Amount blended (% by mass) |
|---|---|
| Purified water | 45.0 |
| Cyclopentasiloxane | 15.0 |
| Butylene glycol | 6.4 |
| Zinc oxide powder in EXAMPLES 1 to 3, COMPARATIVE EXAMPLES 1 and 2 | 15.0 |
| Ethylhexyl methoxycinnamate | 7.5 |
| Bisethylhexyloxyphenol methoxyphenyl triazine | 1.0 |
| PEG-9 polydimethylsiloxyethyl dimethicone | 2.0 |
| PEG-10 dimethicone | 2.0 |
| Methicone | 2.0 |
| Triethoxycaprylylsilane | 0.3 |
| Phenoxyethanol | 0.3 |
| Ethanol | 3.0 |
| Sodium chloride | 0.5 |

The sunscreen cream was applied onto a quartz glass plate so that the application amount reached 2 $mg/cm^2$ and was naturally dried for 15 minutes, thereby forming a coated film on the quartz glass plate.

The spectral transmittance of the coated film in the ultraviolet region was measured at six positions using an SPF analyzer UV-1000S (manufactured by Labsphere, Inc.), and the SPF values and the critical wavelengths were computed using the measurement values. The results are shown in Table 3.

As shown in Table 3, regarding the average value of the SPF values at the six positions, the SPF value of the sunscreen B1 was 100, the SPF value of the sunscreen B2 was 70, the SPF value of the sunscreen B3 was 85, the SPF value of the sunscreen B4 was 53, and the SPF value of the sunscreen B5 was 43.

In addition, the critical wavelength of the sunscreen B1 was 377 nm, the critical wavelength of the sunscreen B2 was 377 nm, the critical wavelength of the sunscreen B3 was 377 nm, the critical wavelength of the sunscreen B4 was 377 nm, and the critical wavelength of the sunscreen B5 was 375 nm.

That is, it was confirmed that the zinc oxide powder which contained the zinc oxide particles in which the minor axes of the primary particles were 35 nm or more and 350 nm or less and the Heywood diameters of the primary particles were 35 nm or more and 400 nm or less and in which the coefficient of variation of the number distribution of the Heywood diameters of the primary particles was 50% or less was excellent in terms of the ultraviolet-shielding properties in the UV-B region (wavelengths: 280 nm to 315 nm) and the UV-A region (wavelength: 315 nm to 400 nm) and had a broad ultraviolet-shielding region.

TABLE 3

|  | SPF value | Critical wavelength |
|---|---|---|
| Sunscreen B1 | 100 | 377 |
| Sunscreen B2 | 70 | 377 |
| Sunscreen B3 | 85 | 377 |
| Sunscreen B4 | 53 | 377 |
| Sunscreen B5 | 43 | 375 |

INDUSTRIAL APPLICABILITY

The zinc oxide powder of the present invention is excellent in terms of the storage stability, and thus the industrial values thereof are significant. The present invention is capable of providing zinc oxide powder being excellent in terms of storage stability and a dispersion, a composition, and a cosmetic which include the zinc oxide powder.

The invention claimed is:

1. Zinc oxide powder, consisting of zinc oxide particles which is formed of primary particles, wherein
   a coefficient of variation of a number distribution of Heywood diameters of the primary particles which form the zinc oxide particles is 15% or more and 50% or less,
   the zinc oxide particles, contain 95% or more of zinc oxide particles (X) in a number distribution of the zinc oxide particles, wherein
the zinc oxide particles (X) are formed of primary particles (I), and
   the primary particles (I) have a minor axis of 35 nm or more and 350 nm or less and have a Heywood diameter of 35 nm or more and 400 nm or less,
   the zinc oxide particles contains 1.5 to 10% of zinc oxide particles (Y), in a minor axis-based number distribution of the primary particles of the zinc oxide particles, wherein
   the zinc oxide particles (Y) are formed of primary particles (II), and
   the primary particles (II) have a minor axis of 35 nm or more and 100 nm or less.

2. The zinc oxide powder according to claim 1, wherein a major axis of the primary particles which form the zinc oxide particles is 50 nm or more and 650 nm or less.

3. The zinc oxide powder according to claim 1, wherein aspect ratios of the primary particles which form the zinc oxide particles are 1.0 or more and 4.0 or less.

4. The zinc oxide powder according to claim 1, wherein a change ratio of a specific surface area of the zinc oxide powder which is obtained after being left to stand at a temperature of 150° C. and a relative humidity of 100% for 24 hours to the specific surface area of the zinc oxide powder which is obtained before being left to stand is 0.9 or more and 1.1 or less.

5. A dispersion, comprising:
the zinc oxide powder according to claim 1; and
a dispersion medium.

6. A composition, comprising:
the zinc oxide powder according to claim 1;
a resin; and
a dispersion medium.

7. A cosmetic, comprising:
the zinc oxide powder according to claim 1.

8. The cosmetic according to claim 7, comprising:
a dispersion medium.

9. The zinc oxide powder according to claim 1, wherein the specific surface area of the zinc oxide powder is 1.5 m$^2$/g or more and 8.0 m$^2$/g or less.

10. The zinc oxide powder according to claim 1, wherein the coefficient of variation of the number distribution of Heywood diameters of the primary particles which form the zinc oxide particles is 15% or more and 40% or less.

11. The zinc oxide powder according to claim 1, wherein at least some of the surface of the zinc oxide particles has been treated with at least one of an inorganic component and an organic component.

12. Zinc oxide powder, comprising:
zinc oxide primary particles,
   wherein the zinc oxide primary particles includes
      95% or more of zinc oxide primary particles (I) in a number-based distribution thereof, wherein the zinc oxide primary particles (I) have a minor axis of 35 nm or more and 350 nm or less and a Heywood diameter of 35 nm or more and 400 nm or less, and
      1.5 to 10% of zinc oxide primary particles (II) in a number-based distribution thereof, wherein the zinc oxide primary particles (II) have a minor axis of 35 nm or more and 100 nm or less,
   wherein
   a coefficient of variation of a number-based distribution of Heywood diameters of the zinc oxide primary particles of the zinc oxide powder is 15% or more and 50% or less.

13. The zinc oxide powder according to claim 12, wherein the zinc oxide primary particles include
   90% or more of zinc oxide primary particles (III), wherein the primary particles (III) have a minor axis of more than 100 nm and 350 nm or less, and
   the primary particles (I) include the primary particles (II) and the primary particles (III).

14. The zinc oxide powder according to claim 1, wherein the zinc oxide particles (X) includes the zinc oxide particles (Y).

15. The zinc oxide powder according to claim 1, wherein the primary particles (I) include the primary particles (II).

16. The zinc oxide powder according to claim 1, wherein the zinc oxide powder consists of the zinc oxide particles (X) and the zinc oxide particles (Y).

* * * * *